United States Patent [19]
Hudgins

[11] Patent Number: 5,319,399
[45] Date of Patent: Jun. 7, 1994

[54] OPTICAL ALIGNMENT DEVICE
[76] Inventor: John S. Hudgins, 601 Shawnee Trail, Blacksburg, Va. 24060
[21] Appl. No.: 884,697
[22] Filed: May 18, 1992
[51] Int. Cl.⁵ .................. A61B 3/028; G02B 5/126; G01B 11/00
[52] U.S. Cl. .................. 351/222; 351/205; 351/208; 351/211; 351/235; 351/237; 351/239; 359/527; 359/534; 359/664; 359/726; 359/732; 356/399
[58] Field of Search .......... 351/239, 237, 243, 203, 351/211, 235, 205, 208, 221, 222, 233, 234, 236; 359/726, 732, 664, 527, 534, 809, 822, 536, 537; 356/153, 399, 138

[56] References Cited
U.S. PATENT DOCUMENTS 2,095,862 10/1937 Frederick et al. .................. 359/534
3,072,010 1/1963 Brill .................. 88/2.6
3,442,567 5/1969 Hansen .................. 359/726
4,660,929 4/1987 Sick .................. 359/534
4,810,073 3/1989 Opheij .................. 359/726

Primary Examiner—Loha Ben
Assistant Examiner—Michael Papalas
Attorney, Agent, or Firm—Michael J. Ram

[57] ABSTRACT

An optical device for aligning an instrument so that active zones in the instrument are the same distance from the plane of a remote object comprising a lens attached to the instrument, the lens having a curved outer surface and a mirrored back surface. When the active zones in the instrument are aligned parallel to the plane of the remote object and the remote object is illuminated, the proper alignment is indicated by light emanating from the object being focused on a preselected spot.

22 Claims, 2 Drawing Sheets

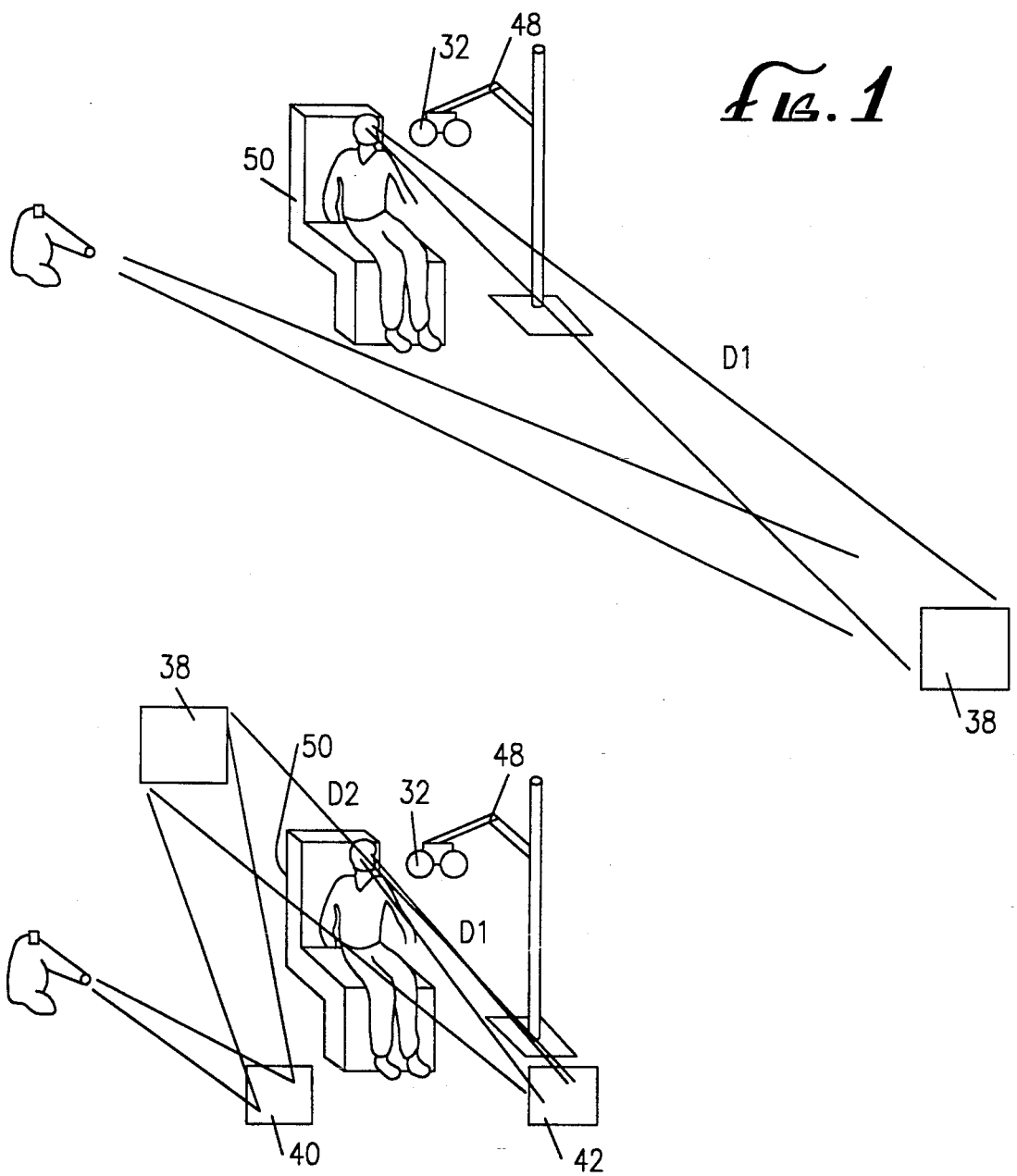

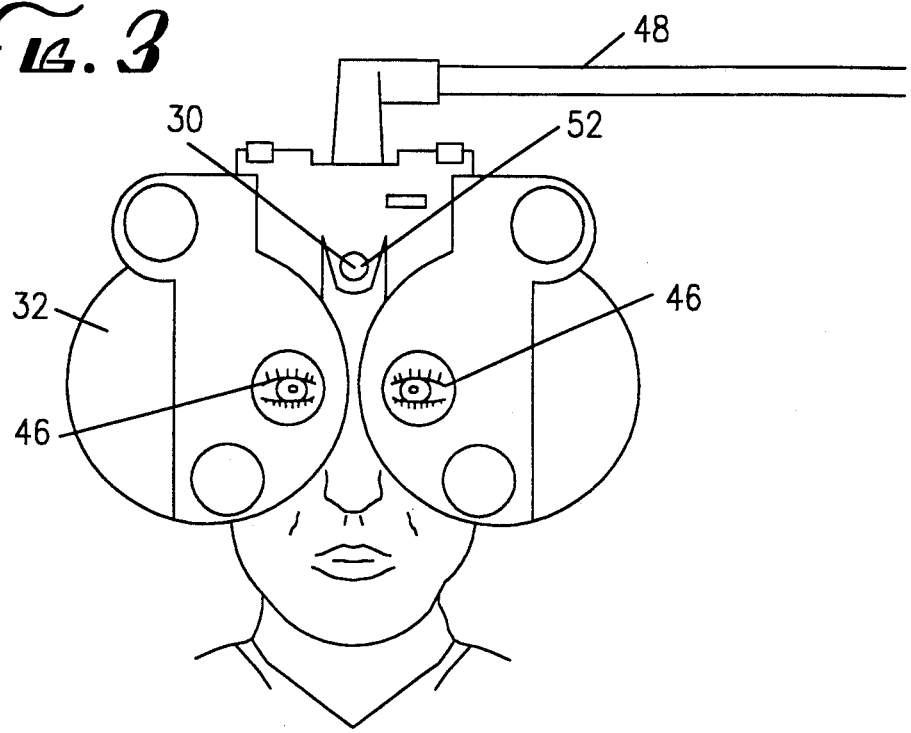
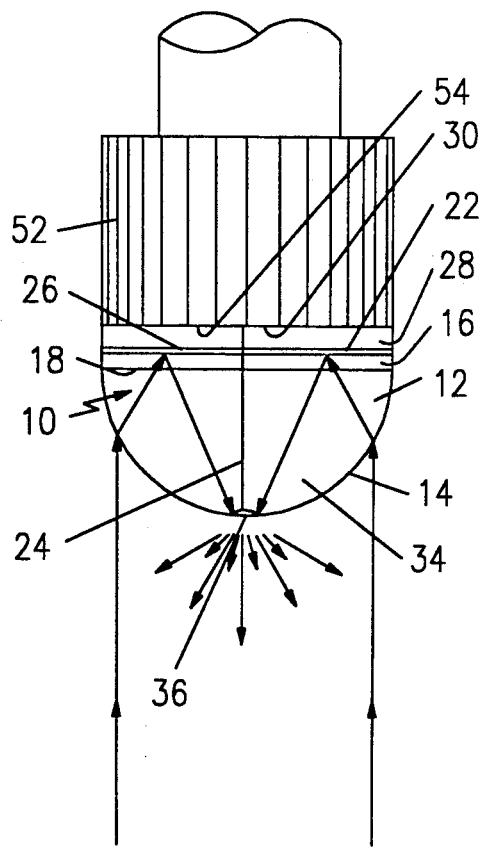
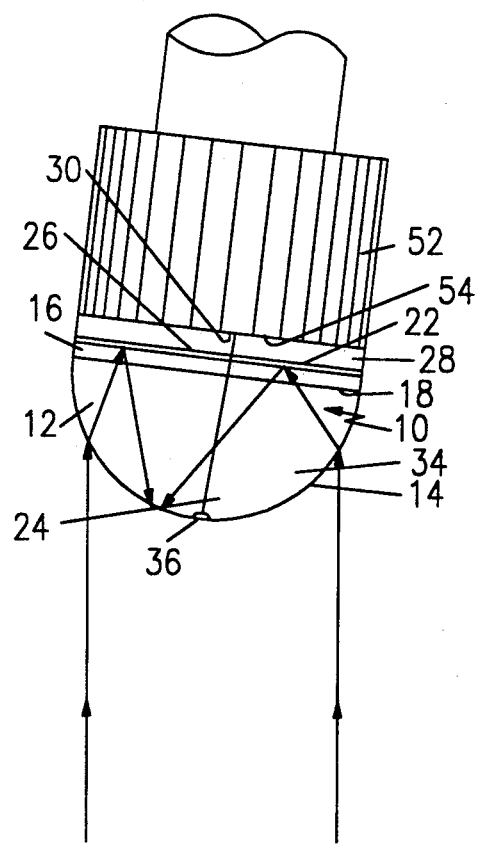

OPTICAL ALIGNMENT DEVICE

BACKGROUND

The present invention relates to a device for aligning two planes spaced a distance from each other parallel relationship to each other. In particular, the present invention relates to a device for aligning optical measuring equipment.

In order to determine the optical correction that a patient requires, the patient views an image located twenty feet away while a series of lenses are positioned in front of the patient's eyes. To select the preferred correction the patient must indicate which lens or combination of lenses results in the clearest image. The lenses or lens combinations, sometimes referred as active zones, are usually located in an instrument referred to as a refractometer, Phoropter being one of the tradenames used on such devices. Different refractometer operators often arrive at slightly different sets of corrective lenses (a different eye glass prescription) for the same patient and the selected prescription may not be the optimum prescription for the patient. Additionally, the same patient may select a different combination of lenses at a different time. This inconsistency in prescription arrived at by operators or at different times can result from several different factors. However, it has been found that a part of the error results from not positioning the two sets of lenses in the refractometer parallel and in axial alignment with the image, i.e., the same distance from the image, being observed by the patient. This is a particularly difficult and time-consuming task as the refractometer and the image are frequently twenty feet apart.

Thus, there is a need for a simple, reliable and accurate method of aligning the refractometer parallel to and in axial alignment with the image. Further, this alignment method should be easily performed in as short a time as possible.

SUMMARY

These needs are met by the device of the present invention.

The device of the present invention comprises an optically clear mirror structure for attachment to the face of the refractometer. The mirror structure has a convex curved outer surface and a flat reflective surface spaced from the curved surface, the space between the two surfaces being a transparent medium. Light coming from the image passes through the curved surface, where it is refracted, and is reflected by the mirrored surface back toward the curved surface. The shape of the surfaces is chosen so that the reflected light is focused on a predetermined point when the refractometer lenses are both parallel and in axial alignment with the image, the predetermined point being located where it can be observed by the equipment operator.

DRAWINGS

These and other features, aspects, and advantages of the present invention will become better understood with reference to the following description, appended claims, and accompanying drawings, where:

FIG. 1 is a perspective view showing a refractometer positioned in a full length refracting lane.

FIG. 2 is a perspective view showing a refractometer positioned in a mirrored lane.

FIG. 3 is a front view showing a refractometer positioned in front of a patient for determining an eyeglass prescription.

FIG. 4 is an enlarged top view of the alignment optic mounted on the forehead brace adjustment knob of the refractometer of FIG. 3, the view illustrating the light ray pattern when the refractometer is properly aligned.

FIG. 5 is an enlarged top view of the alignment optic mounted on the forehead brace adjustment knob of the refractometer of FIG. 3, the view illustrating the light ray pattern when the refractometer is improperly aligned.

DESCRIPTION

FIGS. 1 and 2 show common arrangements used to determine the eye glass prescription of a patient, FIG. 3 shows an instrument for use in the arrangement of FIGS. 1 or 2 positioned on the face of a patient, and FIGS. 4 and 5 depict an exemplary optical alignment device embodying features of the invention applied to the instrument.

The optical device 10 shown in FIGS. 4 and 5 is composed of a lens 12 of an optically clear material having a curved outer surface 14 on a first end. In a preferred embodiment the lens 12 has a flat rear surface 22 perpendicular to an axis 24 through the center of the lens 12. The flat rear surface 22 of the lens 12 is mirrored so that light passing through the curved outer surface 14 will strike the mirrored surface 26 and be reflected back to the curved surface 14. Attached to the flat rear surface 22 is a mounting means 28 for attaching the optical device 10 to a flat surface 30 of an instrument 32 to be aligned. If the lens 12 is a hemisphere it may be necessary to extend the length of the lens 12 by adding a spacer portion 16 to focus the reflected light onto a specified point. In such a case spacer portion 14 is integral with the lens 12 and of the same material has an inner surface 18 spaced to a predetermined distance from the curved surface.

The optical device 10 can be formed from any optically transparent material such as glass or plastic, suitable plastics including polycarbonate, acrylics, polyurethanes, allyl diglycol carbonate. Preferably, the curved outer surface 14 of the optical device 10 is convex. As shown in FIGS. 4 and 5 the optical device 10 is a hemisphere 34. A suitable variation is a spherical section, typically larger than half a sphere. However, depending on the refractive index of the material, the spherical section can be smaller than half a sphere. While use of a spherical surface simplifies calculating the dimensions of the optic, other curved surfaces, such as parabolic, ellipsoidal and aspheric surfaces, or even a concave surface, can also be used to construct the lens 12 of the invention.

Located at or near the curved outer surface 14 of the lens 12 along the optic axis 24 is a small diameter spot 36 which is affected by the light focused thereon. The spot 36 can be made less transparent than the lens by mechanically toughening the surface of the lens, such as by abrading or scoring the surface, chemically modifying the surface, such as by use of a solvent or etchant, or by applying a coating such as a colorant. Alternatively, the spot 36 can be made by applying a light activated material to the surface of the lens. In each instance, when observed by the refractometer operator, the spot 36 will appear to glow or change color when the light is focused on it. In particular, the spot 36 caused to glow by scattering of focused light in incident thereon can be visualized by the operator from numerous locations around the refractometer, including locations removed from the direct line of light incident on the refractometer coming from the eye chart. As explained below, the spot 36 is used to indicate when proper alignment is obtained.

The dimensions of the lens 12 are chosen so that, when properly aligned, light striking the curved outer surfaces 14 is refracted by the surface 14, is reflected by the mirrored surface 26 and is focused to a point on or near the spot 36 (the focal point or focal locus of the lens) where the image appears inverted and greatly reduced in size. The length of the lens 12 (the distance from the center of the curved outer surface 14 to the mirrored surface 26) is chosen to be one half of the focal length of the curved refracting surface.

For a spherical surface, one method of approximating the focal length is the following formula:

$$f = \frac{1}{\frac{1}{u} + \frac{N2 - N1}{r}}$$

where
f = focal length of the optic (in meters)
u = the distance to the object (in meters)
N2 = the index of refraction of the optic material
N1 = the index of refraction of air
r = the radius of curvature of the spherical refracting surface (in meters)

The size of the inverted image is defined by the formula:

$$S_1 = \frac{S_p \times f}{u}$$

where
$S_i$ = the size of the image (in meters)
$S_p$ = The size of image on the eye chart (in meters)
f = the focal length of the refracting surface (in meters)
u = the distance to the image (in meters)

However, other methods of more or less accuracy are known to those skilled in optics.

If the curve on the surface and/or the refractive index of the lens 12 such that the focal point is located within the optic, if desired, the hemisphere 34 can be truncated (the distance from the curved surface 14 to the mirrored surface 26 is shortened) so that the focal point is moved to or nearer to the curved surface 14. Conversely, if the focal point of the lens 12 is in the space in front of the curved surface the lens 12 can be lengthened by adding a straight optically clear spacer portion 16, preferably of the same material as the hemisphere 34 to move the focal point to or nearer to the curved surface 14. Otherwise the image seen at the surface 14 will be unclear or the spot 36 may not receive enough light to respond as desired and the instrument 32 can be difficult to orient. While the optical device 10 can be designed to focus the light directly to a point on the surface doing so can produce an image too small to be easily visualized. Therefore, it can be desirable to focus the light to a point slightly above or below the lens surface so that the image seen at the spot 36 on the surface 14 is slightly enlarged.

The optical device is typically mounted to a surface 30 of an instrument to be aligned, but may be constructed as an integral part of the instrument. The mounting means 28, incorporating either mechanical or adhesive mounting techniques, are used to position the mirrored surface 26 parallel to the surface being aligned. One preferred mounted means is a flat disc or ring 40 having a contact adhesive on its front and rear surfaces.

A primary application of the invention is in the alignment of optical devices (the instrument 32) used to determine the prescription for corrective eye lenses. In order to understand the operation of a device embodying the invention it is first necessary to understand the common techniques for determining the prescription.

Normal vision (20/20 vision) is defined as the ability of a patient to clearly visualize a character having a width of 5 minutes of arc located 20 feet from the eye of the patient. To test the vision of the patient, or to select a lens prescription which will correct the patient's vision to 20/20, the patient is seated facing a flat surface 38 located a fixed distance from the patient. The patient then observes a chart of symbols mounted on or projected on the surface 38.

In the most preferred arrangement the spacing is chosen so that the distance $D_1$ of the eyes of the seated patient are twenty feet from the image on the surface 38, as shown in FIG. 1. However, in many cases, because of space limitations, a twenty foot distance is not available. In such an instance, a shorter distance $D_1$ can be used by positioning a series of mirrors parallel to each other so that the patient observes an image reflected onto the surface 38. FIG. 2 shows an arrangement using a first mirror 40, a second mirror 42 and surface 38. Set up in this manner, the image is projected onto the first mirror 40, it is reflected from the first mirror 40 to the surface 38, and the image projected onto the surface 38 is then reflected by the second mirror 42, the image traveling a distance $D_2$ from the surface 38 to the second mirror 42. The patient views the image in the second mirror 42 which is a distance $D_1$ (less than twenty feet) from the patient. However, the positioning of the mirror 42 and the surface 38 is selected so that the total distance the image travels from the surface 38 to the patient ($D_2$ plus $D_1$) is twenty feet.

To determine a corrective prescription, different viewing lenses 46 or combinations of viewing lenses 46 are placed directly in front of the patients eyes. While individual viewing lenses 46 can be used, more typically an instrument 32, called a refractometer is utilized. This instrument 32 has two sets of viewing lenses 46, one set for each eye, each set containing several different viewing lenses 46 of different powers. The first set of viewing lenses 46 is located in a plane parallel to the plane of the second set of viewing lenses 46. Preferably, both sets of viewing lenses 46 are in the same plane. The refractometer, mounted on an articulated arm 48 between the patient and the image on the surface 38 being observed, is positioned so that each set of viewing lenses 46 is in front of and in the visual axis of the eye being tested. The sets of viewing lenses 46 must be parallel to the image of surface 38 and in axial alignment with the image of surface 38.

To conduct the vision test the patient is seated in the refracting chair 50 facing the mirror 42. The equipment operator places the refractometer in front of the patient (FIG. 3) and the spacing between the two sets of viewing lenses 46 is adjusted so that the right eye of the patient is looking through the center of the right viewing lens 46 and the left eye of the patient is looking through the center of the left viewing lens 46. The refractometer must also be positioned so the plane of the viewing lenses 46 is parallel to the plane of the image being viewed and an imaginary line through the center of each set of viewing lenses 46 is on the same plane as a center line across the image. This requires adjustment of the refractometer in the three planes. If the alignment is not correct, coma and astigmatism of oblique incidence, two types of optical aberration, can result, causing an erroneous prescription.

While operators believe that they are competent to properly align the refractometer, some inconsistencies can be eliminated by improving the alignment of the refractometer with the wall chart.

This source of error is eliminated by using the optical device 10 of the invention to align the refractometer. FIG. 4 is an enlarged top view of the invention attached to the forehead brace adjustment knob 52. Light from the image striking the lens 12 is refracted at the curved outer surface 14 and transmitted through the optically transparent material onto the mirrored surface 26 spaced from the curved outer surface 14. The light is then reflected from the mirrored surface 26 back through the optical material of the lens 12.

As a result of the dimensions of the lens 12 and the shape of the curved outer surface 14 of the lens 12 the light is focused to a singular point (the focal point or focal locus of the lens 12). In a preferred embodiment, the point of focus of the light is located at the spot 36. Because a major portion of the light incident on the lens 12 is focused to a single point, or region which scatters the light, this focal point is much brighter to an observer then the surrounding area. If the location of the focal point coincides with the spot 36, such as a colored dot or a translucent surface, the spot 36 appears to glow.

FIG. 4 is a ray diagram showing how the incident light is focused to a preselected spot 36 on the surface of the lens 10 when the mirrored surface 26 of the lens 12 is positioned parallel to the plane of an image of a distant surface 38. FIG. 5 is a ray diagram showing how the incident light is focused to a different point when the plane of the mirrored surface 26 is not parallel to the plane of the image, or, in the situation where the mirrored surface 26 is parallel to the plane of the viewing lens 46, the viewing lenses 46 are not parallel to the plane of the image.

A properly constructed refractometer has the two sets of viewing lenses 46 located in the same plane. Additionally, the plane of the viewing lenses 46 in the refractometer is usually parallel to at least one surface on the exterior of the device. In particular, the front surface 54 of the forehead brace adjustment knob 52 is usually parallel to the plane of the viewing lenses 46. FIGS. 4 and 5 show the optical device 10 mounted on the front surface 54 of the forehead brace adjustment knob 52. As a result, when the mirrored surface 26 of the alignment device is parallel to the image, as evidenced by the focusing of the incident light on the preselected spot 36 located on the optic surface 14, the viewing lenses 46 are also parallel to the image and thus properly aligned. However, it is not necessary that lens 12 be mounted to a surface parallel to the viewing lenses 46. The lens 12 can be formed with the mounting means 28 attached to other than the flat rear surface 22 as long as the plan of the mirrored surface 26 is parallel to the viewing lenses 46. Alternatively, the lens 12 can have the mirrored surface 26 positioned so that when mounted on the refractometer the desired indicia of alignment is obtained, i.e., at an angle to the axis of the lens so that when aligned, the selected spot 36 is visualized.

In order to more clearly define the invention, the following example of a device embodying features of the invention is set forth. This example is illustrative only and is not limiting as to the scope of the invention.

EXAMPLE 1

A spherical lens with a radius of 1.0 cm was formed from a polymethyl methacrylate plastic having a refractive index of 1.491. The distance from the center of the curved surface to the mirrored rear surface (one-half of the focal length f) was calculated using the formula above to be 1,015, 0.015 cm greater than the radius of the hemisphere. When the spherical lens was placed on the forehead brace adjustment knob of a refractometer positioned 6 meters from a projected image and the refractometer properly positioned the light from the projected image formed an image at a predetermined opaque spot formed on the center of the surface of the lens.

Without the assistance of the alignment device, aligning the refractometer is time-consuming and not necessarily accurate. The positioning device allows alignment to be readily accomplished in a short period of time. Additionally, the device of the invention allows the correct alignment of the refractometer to be observed by an operator without the operator standing directly in front of the refractometer, the glowing spot being observable from many locations.

Although the present invention has been described in considerable detail with reference to a certain preferred version and use thereof, other versions and uses are possible. For example, various different optical materials can be used. All that is necessary is that the dimensions be varied to reflect the different refractive indices of these materials. It is also possible to eliminate the spacer if the proper refractive index is chosen. Further, the device is described as mounted on the forehead brace adjustment knob. Other locations on the refractometer are also possible or the knob can be fabricated with the optical device permanently mounted thereto so that the device can be applied to a refractometer by changing the adjustment knob. Alternatively, the curved surface of the optic does not have to be spherical; aspherical surfaces or elliptical surfaces are also useful. The invention also contemplates locating the alignment spot at a point other than on the surface of the lens at the intersection of the lens axis. For example, the alignment spot can be located inside the lens, at a different location on the surface of the lens or at a preselected location spaced from the lens. The different locations of the alignment spot can be obtained by varying the shape of the curved surface or the length of the lens.

While the alignment optic has been described in the context of properly positioning a refractometer it is also contemplated that the alignment optic can be used to align any two planer surfaces parallel to each other. Therefore, the spirit and scope of the appended claims should not be limited to the description of the preferred versions contained herein.

What is claimed is:

1. A lens for orienting a portion of an instrument so as to be parallel to and in axial alignment with a planar surface located a distance from the instrument, the lens being formed from an optically transparent material, the lens further having a curved outer surface and a reflective rear surface, such that light penetrating the curved outer surface will impinge on the reflective rear surface and be reflected back toward the curved outer surface, said lens focusing light reflected from the planar surface at a preselected spot visible to the operator when the instrument is in alignment, said preselected spot is located on the curved outer surface, the lens being attachable to the instrument with the reflective rear surface at a predetermined angle to the portion of the instrument being oriented.

2. The lens of claim 1 wherein the instrument is a refractometer and the portion of the instrument to be oriented is a first lens system and a second lens system, the first lens system being located in a first plane and the second lens system being located in a second plane, the first plane and the second plane being parallel to each other.

3. The lens of claim 1 wherein the curved outer surface is a convex curved surface.

4. The lens of claim 1 wherein the optically transparent material is formed to the shape of a section of a sphere, the section of the sphere having an axis passing through the center thereof.

5. The lens of claim 4 wherein the reflective rear surface is a flat surface perpendicular to the axis passing through the center of the section of the sphere.

6. The lens of claim 5 wherein the section of the sphere is a hemisphere.

7. The lens of claim 6 wherein the hemisphere has a radius of 1.0 cm and the optically clear material has a refractive index of 1.491.

8. The lens of claim 1 further including mounting means for attaching the lens to the instrument.

9. A device for orienting the lenses mounted in a refractometer so as to be parallel to and in axial alignment with an illuminated image located on a flat surface a distance from the refractometer, the device comprising:

(a) a mirror for attachment to the refractometer, said mirror having a reflecting surface and a curved refracting surface, and (b) means to affix the mirror to the refractometer so that said reflecting surface of said mirror is oriented at a predetermined angle to the plane defined by the lenses of the refractometer, the contour of the curved refracting surface being chosen so that light emanating from the illuminated image impinging on the curved surface will be refracted toward the flat surface and reflected from the flat surface back toward the curved surface, in a manner such that a substantial portion of the reflected light will converge at a preselected point.

10. The device of claim 9 wherein the mirror is a hemisphere with a flat base, the hemisphere having an axis passing through the center of the hemisphere and the center of the base, the base being perpendicular to the axis, the curved surface of the hemisphere being the refracting surface and the base being the reflecting surface.

11. The device of claim 10 further including a translucent spot located at the intersection of the surface of the hemisphere and the axis.

12. The device of claim 11 wherein a substantial portion of the reflected light converges to a point at at or close to the location of said translucent spot so that said translucent spot is illuminated to an observer located in the vicinity of the refractometer.

13. A system for aligning a device with a distant surface, the device having a pair of spaced apart active zones, the system comprising:

(a) means for providing light directed toward the device from the distant surface, and (b) lens means on the device for focusing the light toward a selected focal locus so that the light is focused on the selected focal locus when the active zones are substantially the same distance from the surface, and wherein the light is not focused on the selected focal locus when the active zones are not at substantially the same distance from the surface.

14. The device of claim 13 wherein the device is a refractometer and the spaced apart active zones are a first lens set and a second lens set enclosed within the refractometer.

15. The device of claim 13 wherein the means for providing light directed to the device is a bulb focused to project light on the distant surface.

16. The device of claim 13 wherein the means for providing light directed to the device is a projector which focuses an illuminated image onto a distant surface.

17. The device of claim 13 wherein the lens means is a section of a sphere having a flat reflective base, the selected focal locus being a predetermined point at at or close to the curved surface of the section of the sphere.

18. The device of claim 14 herein the section of the sphere is a hemisphere.

19. The device of claim 18 wherein the hemisphere has a diameter of 1.0 cm and a refractive index of 1.491.

20. The device of claim 13 wherein the lens means is fabricated from an optically clear material selected from the group consisting of glass, polycarbonate polymer, acrylic plastic, polyurethane polymer and allyl diglycol carbonate polymer.

21. The device of claim 13 wherein the selected focal locus appears to an observer in the vicinity of the device to glow when the active zones are substantially in alignment with the distant surface.

22. A lens for orienting a portion of an instrument so as to be parallel to and in axial alignment with a planar surface located a distance from the instrument, the lens being formed from an optically transparent material, the lens further having a curved outer surface and a reflective rear surface, such that light penetrating the curved outer surface will impinge on the reflective rear surface and be reflected back toward the curved outer surface, said lens focusing light reflected from the planar surface at a preselected spot visible to the operator when the instrument is in alignment, said preselected spot being within said lens, the lens being attachable to the instrument with the reflective rear surface at a predetermined angle to the portion of the instrument being oriented.

* * * * *